United States Patent [19]

Toth

[11] 4,381,409
[45] Apr. 26, 1983

[54] PROCESS FOR THE PRODUCTION OF 2,4-DINITROANILINES

[75] Inventor: Istvan Toth, Bottmingen, Switzerland

[73] Assignee: Sandoz Ltd., Basel, Switzerland

[21] Appl. No.: 301,979

[22] Filed: Sep. 14, 1981

[30] Foreign Application Priority Data

Sep. 18, 1980 [DE] Fed. Rep. of Germany ....... 3035140

[51] Int. Cl.³ .............................................. C07C 85/04
[52] U.S. Cl. .................................... 564/406; 564/412; 564/441
[58] Field of Search ............................... 564/406, 412

[56] References Cited

U.S. PATENT DOCUMENTS 2,491,481 12/1949 Dickey ............................ 564/406 X
4,102,927 7/1978 Volkwein et al. ................... 564/406

FOREIGN PATENT DOCUMENTS 50-46633 4/1975 Japan .................................... 564/412

*Primary Examiner*—John Doll
*Attorney, Agent, or Firm*—Gerald D. Sharkin; Richard E. Vila; Thomas C. Doyle

[57] ABSTRACT

A method for the preparation of 2,4-dinitroaniline from 1-chloro-2,4-dinitrobenzene comprising adding ammonia to melted 1-chloro-2,4-dinitrobenzene in such dosages that the temperature of the mixture does not exceed 120° C. and that the pressure does not exceed 3 bar. 6-halo-2,4-dinitroaniline may be produced from the so formed 2,4-dinitroaniline by neutralizing the suspension containing the 2,4-dinitroaniline with acid to give a pH of from the 6-halo-2,4-dinitroaniline. The 6-halo 2,4-dinitroaniline is useful in the preparation of dyestuffs.

12 Claims, No Drawings

PROCESS FOR THE PRODUCTION OF 2,4-DINITROANILINES

The invention relates to an improved method for the preparation of 2,4-dinitroaniline and an improved method for the preparation of 6-halo 2,4-dinitroaniline which is useful in the preparation of azo dyestuffs.

One known method for the preparation of 2,4-dinitroaniline from 1-chloro-2,4-dinitrobenzene comprises heating a mixture of 1-chloro-2,4-dinitrobenzene and ammonia to about to 70° C. and during the exothermic reaction that occurs cooling the mixture so that the temperature does not exceed 120° C.

Another known method comprises heating a mixture of 1-chloro-2,4-dinitrobenzene, ammonia and chlorobenzene to 150° C.

Still a further known method for preparing 2,4-dinitroaniline is to take 300–400% theory of aqueous ammonia (with respect to 1-chloro-2,4-dinitrobenzene) and pump in melted 1-chloro-2,4-dinitrobenzene while maintaining the reaction temperature between 60° and 90° C.

All these known methods however have the disadvantage that they must be carried out in an autoclave.

Further, it has been found that by taking 1-chloro-2,4-dinitrobenzene and adding the aqueous ammonia solution in a single dose a dark unsuitable reaction product was formed after stirring for a long time at a high temperature.

The invention provides a method for the preparation of 2,4-dinitroaniline from 1-chloro-2,4-dinitrobenzene comprising adding ammonia to melted 1-chloro-2,4-dinitrobenzene in such dosages that the temperature of the mixture does not exceed 120° C. and that the pressure does not exceed 3 bar.

Preferably the temperature is in the range 80°–120° C., more preferably, 95°–120° C., most preferably 100°–110° C.

Preferably the pressure is in the range 1.1 to 3 bar more preferably 1.2 to 2 bar most preferably 1.2 to 1.8 bar.

Further the invention provides a method for the preparation of 6-halo-2,4-dinitroaniline from 1-chloro-2,4-dinitrobenzene comprising adding ammonia to melted 1-chloro-2,4-dinitrobenzene in such dosages that the temperature of the mixture does not exceed 120° C. and that the pressure does not exceed 3 bar, neutralising the suspension so formed by the addition of mineral or organic acid to give a pH of about 7; and halogenating the resulting solution to form 6-halo-2,4-dinitroaniline.

Melting of the 1-chloro-2,4-dinitrobenzene may be effected by heating, preferably at a temperature in the range 70° to 80° C.

The addition of ammonia is carried out with vigorous stirring whilst continuously monitoring the temperature and pressure (preferably automatically).

Preferably the ammonia solution added is a 10% to 25% more preferably 25% aqueous solution.

Preferably the temperature of the reaction mixture is allowed to rise from 70° to the reaction temperature (which is preferably in the range 80°–120° C.) due to the exothermic process and is held at a temperature under 120° C. by cooling.

Preferably the ammonia solution is added to 1-chloro-2,4-dinitrobenzene in a mole ratio of at least 2:1 preferably in the range 2.5:1–3.0:1 respectively.

It has been found that after the addition of ammonia and the formation of a solution containing 2,4-dinitroaniline, the 6-halo-2,4-dinitroaniline can be prepared by neutralising the reaction mixture containing 2,4-dinitroaniline by the addition of mineral acid (for example hydrochloric or sulphuric acid) and then halogenating according to known methods at elevated temperature (for example 60°–90° C.) preferably with chlorine or bromine. It has been found advantageous to wet grind the reaction mixture (a suspension containing 2,4-dinitroaniline) prior to halogenation.

The end of each of the reactions is determinable by thin layer chromatography.

The 6-halo-2,4-dinitroaniline, after filtering and washing with water and generally without further purification, is ready for use in the preparation of dyestuffs.

Halogen as used herein refers to chlorine or bromine.

The term "ammonia" as herein used means gaseous ammonia or aqueous ammonia solution.

The invention will now be illustrated by means of the Examples in which all parts and percentages are by weight and all temperatures are in degrees Centigrade.

EXAMPLE 1

202.5 Parts of 1-chloro-2,4-dinitrobenzene is placed in a well-sealed container. After heating to 70° whereupon the 1-chloro-2,4-dinitrobenzene melts, approximately 200 parts of an approximately 25% solution of ammonia is pumped into the container with very intensive stirring so that the temperature rises to 100°. The reaction is completed at this temperature and with a pressure of from 1.2 to 2 Bar. The addition of ammonia solution is effected with temperature and pressure control. The progress of the reaction can be determined by the amount of ammonia solution used. Additionally the end point of the reaction may be determined by thin layer chromatography. The reaction is finished when the 2,4-dinitroaniline so produced contains less than 0.15% of the starting material (1-chloro-2,4-dinitrobenzene). The reaction time is about 16 hours.

The pH of the suspension is adjusted to 7 by the addition of mineral acid and after the solution of 300 parts of water is wet ground for 2–3 minutes. Finally the reaction mixture is treated with 165 parts of bromine at 60°–90° and the reaction time is 1 to 1½ hours. The end of the bromination can be detected by thin layer chromatography.

Excess bromine is removed by blowing a gentle stream of air through the reaction mixture. The yellow suspension is filtered whilst warm (at about 80°) and washed with 4000 parts of cold water until the washings are neutral. The product is dried at 120°.

The yield of 6-bromo-2,4-dinitroaniline is 93% of theory with a purity of 98.5%.

EXAMPLE 2

202.5 Parts of 1-chloro-2,4-dinitrobenzene is placed in 100 parts of water and is converted to 2,4-dinitroaniline with ammonia solution according to the method of Example 1. The 2,4-dinitroaniline is then brominated also according to the method of Example 1.

The yield of 6-bromo-2,4-dinitroaniline is 93.3% of theory with a purity of 98.6%.

EXAMPLE 3

202.5 Parts of 1-chloro-2,4-dinitrobenzene is placed in 100 parts of water and 1 part of emulsifier (Tween 80 a trade mark) and is converted to 2,4-dinitroaniline with ammonia solution according to the method of Example 1. Then the 2,4-dinitroaniline is brominated according to the method of Example 1. The reaction time is 10 hours.

The yield of 6-bromo-2,4-dinitroaniline is 94% of theory with a purity of 99%.

EXAMPLE 4

The method of Example 3 is performed except that instead of brominating 2,4-dinitroaniline it is chlorinated with 75 parts of chlorine.

The yield of 6-chloro-2,4-dinitroaniline is 95% of theory with a purity of 99%.

EXAMPLE 5

The method of Example 1 is performed except that a 10% ammonia solution is used to prepare 2,4-dinitroaniline. The yield of 6-bromo-2,4-dinitroaniline is 94% of theory with a purity of 98.8%.

What is claimed is:

1. In a process for the production of 2,4-dinitroaniline by reacting 1-chloro-2,4-dinitrobenzene with ammonia, the improvement which comprises adding the ammonia to melted 1-chloro-2,4-dinitrobenzene in such dosages that the temperature of the reaction mixture does not exceed 120° C. and the pressure does not exceed 2 bar.

2. A process according to claim 1 comprising the additional steps of neutralising the resulting suspension of 2,4-dinitroaniline by the addition of mineral or organic acid to give a pH of about 7; and halogenating the resulting solution to form 6-halo-2,4-dinitroaniline.

3. A process according to claim 1 or claim 2 in which the temperature of the reaction mixture of melted 1-chloro-2,4-dinitrobenzene and ammonia is in the range 80°-120° C.

4. A process according to claim 3 in which said temperature is in the range of 100°-110° C.

5. A process according to claim 1 wherein the pressure is in the range 1.2 to 2 bar.

6. A process according to claim 5 wherein the temperature of the reaction mixture is in the range 80°-120° C.

7. A process according to claim 1 or claim 2 in which the pressure of the 1-chloro-2,4-dinitrobenzene and ammonia solution is 1.2 to 1.8 bar.

8. A process according to claim 1 or claim 2 in which the ammonia added is a 10% to 25% aqueous ammonia solution.

9. A process according to claim 1 or claim 2 in which the total addition of ammonia is such as to produce a mole ratio of ammonia to 1-chloro-2,4-dinitrobenzene of at least 2:1.

10. A process according to claim 6 wherein the amount of ammonia added is such that the mol ratio of ammonia to 1-chloro-2,4-dinitrobenzene is at least 2:1.

11. A process according to claim 5 wherein the reaction is carried out in the absence of an autoclave.

12. A process according to claim 10 wherein the reaction is carried out in the absence of an autoclave.

* * * * *